United States Patent
Krüger et al.

[11] Patent Number: 5,750,526
[45] Date of Patent: May 12, 1998

[54] PYRIDO [1,2,3-DE]QUINOXALINE DERIVATIVES, PROCESS FOR THEIR PRODUCTION AND THEIR USE IN PHARMACEUTICAL AGENTS

[75] Inventors: Martin Krüger; Werner Seelen; Lechoslaw Turski, all of Berlin, Germany

[73] Assignee: Schering Aktiengesellschaft, Berlin, Germany

[21] Appl. No.: 535,250

[22] PCT Filed: Apr. 28, 1994

[86] PCT No.: PCT/DE94/00494

§ 371 Date: Dec. 27, 1995

§ 102(e) Date: Dec. 27, 1995

[87] PCT Pub. No.: WO94/25472

PCT Pub. Date: Nov. 10, 1994

[30] Foreign Application Priority Data

Apr. 28, 1993 [DE] Germany .................. 43 14 593.0

[51] Int. Cl.⁶ .................................................. A61K 31/495
[52] U.S. Cl. ........................ 514/250; 544/337; 544/344
[58] Field of Search ................................ 544/337, 344; 514/250

[56] References Cited

FOREIGN PATENT DOCUMENTS 9015058 12/1990 WIPO.
9308188 4/1992 WIPO.

OTHER PUBLICATIONS

Alfred Richardson, Jr., "The Chemistry of 7-Aminoindoline and Certain Pyrrolo— and Pyrido[1,2,3-de]quinoxalines," *The Journal of Organic Chemistry*, vol. 30, No. 7, pp. 2580–2593, Jul. 1965.

*Primary Examiner*—Matthew V. Grumbling
*Attorney, Agent, or Firm*—Millen, White, Zelano, & Branigan, P.C.

[57] ABSTRACT

Pyrido[1,2,3-de]quinoxaline derivatives of formula I

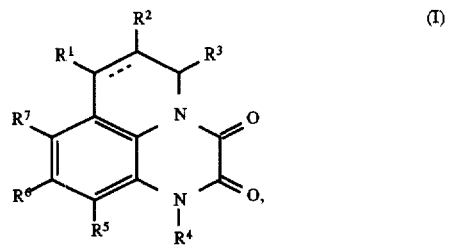

in which $R^1$, $R^2$ and $R^3$ each mean hydrogen, —POXY, halogen or —COR, $R^4$ means hydrogen or OH, $R^5$, $R^6$ and $R^7$ are the same or different and mean hydrogen, halogen, nitro, $NR^{12}R^{13}$, cyano, $CF_3$, $C_{1-6}$ alkyl, $C_{1-4}$ alkoxy, or $R^5$ and $R^6$ or $R^6$ and $R^7$ represent a fused benzene ring, and means a single or double bond, are described as well as their production and use in pharmaceutical agents.

4 Claims, No Drawings

PYRIDO [1,2,3-DE]QUINOXALINE DERIVATIVES, PROCESS FOR THEIR PRODUCTION AND THEIR USE IN PHARMACEUTICAL AGENTS

This is a national stage application filed under 35 U.S.C. §371 of PCT/DE94/00494, filed on Apr. 28, 1994.

The invention relates to pyrido[1,2,3-de]quinoxaline derivatives, their production and use in pharmaceutical agents.

It is known that quinoxaline derivatives have an affinity to the quisqualate receptors and, because of the affinity, are suitable as pharmaceutical agents for the treatment of diseases of the central nervous system.

It has now been found that the compounds according to the invention are suitable to counteract the hyperactivity of excitatory amino acids.

The compounds according to the invention have formula I

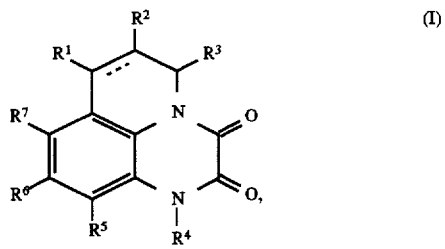

in which $R^1$, $R^2$ and $R^3$ each mean hydrogen, —POXY, halogen or —COR, $R^4$ means hydrogen or OH, $R^5$, $R^6$ and $R^7$ are the same or different and mean hydrogen, halogen, nitro, $NR^{12}R^{13}$, cyano, $CF_3$, $C_{1-6}$ alkyl, $C_{1-4}$ alkoxy or $R^5$ and $R^6$ or $R^6$ and $R^7$ represent a fused benzene ring, and

means a single or double bond, and

X and Y are the same or different and mean hydroxy, $C_{1-6}$ alkoxy, —O—$(CH_2)_n$—O—, $C_{1-4}$ alkyl or $NR^9R^{10}$ and n is 1, 2 or 3 and R means hydroxy, $C_{1-6}$ alkoxy or $NR^9R^{10}$ and $R^9$ and $R^{10}$, $R^{12}$ and $R^{13}$ are the same or different and mean hydrogen, —CO—$C_{1-6}$ alkyl, phenyl or $C_{1-6}$ alkyl, which can be optionally substituted with $C_{1-4}$ alkoxy or with an amino group that is optionally mono- or disubstituted with $C_{1-4}$ alkyl, or together with the nitrogen atom can form a saturated 5- to 7-membered heterocycle, which can contain another oxygen, sulfur or nitrogen atom and can optionally be substituted or form an unsaturated 5-membered heterocycle, which can contain 1–3N atoms and can be substituted, as well as their isomers or salts.

The compounds of general formula I also contain the possible tautomeric forms and comprise all possible isomers, and, if a chiral center is present, the racemates or enantiomers.

Alkyl is to be understood to mean respectively a straight-chain or branched alkyl radical, such as, for example, methyl, ethyl, propyl, isopropyl, butyl, isobutyl, sec-butyl, tert-butyl, pentyl, isopentyl, hexyl.

Halogen is to be understood to mean respectively fluorine, chlorine, bromine and iodine.

If $R^9$, $R^{10}$ and/or $R^{12}$ and $R^{13}$ together with the nitrogen atom form a saturated heterocycle, then, for example, piperidine, pyrrolidine, morpholine, thiomorpholine, hexahydroazepine or piperazine are meant. The heterocycle can be substituted one to three times with $C_{1-4}$ alkyl or aryl such as phenyl. For example, N-methylpiperazine, N-phenylpiperazine, 2,6-dimethylmorpholine can be mentioned.

If $R^9$, $R^{10}$ and $R^{12}$, $R^{13}$ together with the nitrogen atom form an unsaturated heterocycle, then, for example, imidazole, pyrazole, pyrrole and triazole can be mentioned, which can be substituted once to twice with cyano, $C_{1-4}$ alkyl, phenyl or $CO_2C_{1-6}$ alkyl.

The physiologically compatible salts of organic and inorganic bases are suitable as salts, such as, for example, the readily soluble alkali and alkaline-earth salts, as well as N-methylglucamine, dimethylglucamine, ethylglucamine, lysine, 1,6-hexadiamine, ethanolamine, glucosamine, sarcosine, serinol, tris-hydroxymethylaminomethane, aminopropanediol, Sovak base, 1-amino-2,3,4-butanetriol and the physiologically compatible salts of organic and inorganic acids, such as HCl, HBr, $H_2SO_4$, phosphoric acid, citric acid, tartaric acid, sulfonic acids, i.a.

The compounds of formula I as well as their physiologically compatible salts can be used as pharmaceutical agents because of their affinity to the AMPA receptors. Because of their action profile, the compounds according to the invention are suitable for the treatment of diseases that are caused by hyperactivity of excitatory amino acids, such as, for example, glutamate or aspartate. Since the new compounds act as antagonists of excitatory amino acids and show a high specific affinity to the AMPA receptors, by displacing the radioactively-labeled specific agonist (RS)-α-amino-3-hydroxy-5-methyl-4-isoxazolpropionate (AMPA) from the AMPA receptors, they are especially suitable for the treatment of those diseases that are affected by the receptors of excitatory amino acids, especially the AMPA receptor.

According to the invention, the compounds can be used for the treatment of neurological and psychiatric disorders that are triggered by the overstimulation of the AMPA receptor. The neurological diseases that can be treated functionally and preventatively include neurodegenerative disorders, for example, such as Parkinson's disease, Alzheimer's disease, Huntington chorea, amyotrophic lateral sclerosis and olivopontocerebellar degeneration. According to the invention, the compounds can be used for the prevention of postischemic cell destruction, cell destruction after cerebral trauma, in the case of a stroke, hypoxia, anoxia and hypoglycemia and for the treatment of senile dementia, multiinfarct dementia as well as epilepsy and muscle spasms. The psychiatric diseases include anxiety conditions, schizophrenia, migraine, conditions of pain and sleep disorders, as well as the treatment and prevention of the withdrawal symptoms after drug abuse as well as in alcohol, cocaine, benzodiazepine or opiate withdrawal.

For use of the compounds according to the invention as pharmaceutical agents, the latter are brought into the form of a pharmaceutical preparation, which, besides the active ingredient for enteral or parenteral administration, contains suitable pharmaceutical, organic or inorganic inert vehicles, such as, for example, water, gelatin, gum arabic, lactose, starch, magnesium stearate, talc, vegetable oils, polyalkyleneglycols, etc. The pharmaceutical preparations can be in solid form, for example, as tablets, coated tablets, suppositories, capsules or in liquid form, for example, as solutions, suspensions or emulsions. Moreover, they optionally contain adjuvants such as preservatives, stabilizers, wetting agents or emulsifiers, salts for changing the osmotic pressure or buffers.

Especially suitable for parenteral use are injection solutions or suspensions, in particular aqueous solutions of the active compounds in polyhydroxyethoxylated castor oil.

Surface-active adjuvants, such as salts of bile acids or animal or vegetable phospholipids, but also their mixtures as well as liposomes or their components, can also be used as vehicle systems.

Especially suitable for oral use are tablets, coated tablets or capsules with talc and/or hydrocarbon vehicles or binders, such as, for example, lactose, corn or potato starch. The use can even take place in liquid form, such as, for example, as juice, to which a sweetener is optionally added.

The dosage of the active ingredients can vary depending on method of administration, age and weight of the patient, type and severity of the disease to be treated and similar factors. The daily dose is 0.5–1000 mg, preferably 50–200 mg, and the dose can be administered as a single dose to be administered once or subdivided into 2 or more daily doses.

The production of the compound according to the invention takes place according to methods known in the art. For example, compounds of formula I are attained in that a) a compound of formula II

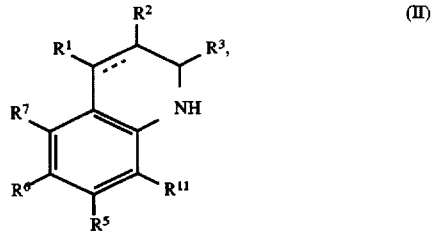

in which $R^{11}$ is H, $NO_2$ or —NH—$R^4$ and $R^1$ to $R^7$ have the above-mentioned meaning, is reacted with oxalic acid or reactive oxalic acid derivatives and is optionally cyclized after introduction and reduction of the $NO_2$ group and, if $R^1$, $R^2$ and/or $R^3$ mean halogen, is optionally reacted or carbonylated with XYP—O—$C_{1-4}$ alkyl or b) a compound of formula III

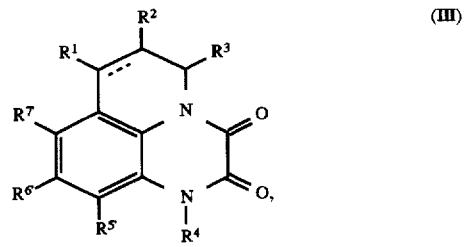

in which $R^1$ to $R^4$ have the above-mentioned meaning and $R^{5'}$, $R^{6'}$ or $R^{7'}$ mean hydrogen or an electron-attracting group, is halogenated or nitrated and then optionally an ester group is saponified or an acid group is esterified or amidated or a nitro group is reduced to the amino group or the amino group is alkylated or acylated or an amino group is exchanged for halogen or cyano or a nitro group or halogen is introduced or nucleophilically substituted or the isomers are separated or the salts are formed.

The cyclization of the compounds of formula II takes place in one stage or else in two stages with oxalic acid or a reactive oxalic acid derivative. Regarded as preferable is the two-stage process in which the diamine is reacted with an oxalic acid derivative such as oxalic ester semi-chloride or reactive oxalic acid imidazolide derivatives in polar solvents such as cyclic or acyclic ethers or halogenated hydrocarbons, for example, tetrahydrofuran, diethyl ether or methylene chloride in the presence of a base such as organic amines, for example, triethylamine, pyridine, Hünig base or dimethylaminopyridine. The subsequent cyclization can be performed in a basic or else acidic manner, but preferably in an acid environment, and alcohol can be added to the solvent.

Alkali hydrides such as NaH, which are used in inert solvents such as hydrocarbons and ethers, also represent suitable bases for the two-stage process.

If $R^{11}$ in the compounds of formula II means hydrogen, then nitration can be performed in the usual way after the acylation with the reactive oxalic acid derivative. Of the known nitration methods, the reaction with sodium nitrate in trifluoroacetic acid or with nitronium tetrafluoroborate in chlorinated hydrocarbons is especially suitable. The reduction of nitro group $R^{11}$ takes place in the usual way catalytically or by reduction with iron powder in acetic acid at higher temperature or else with sodium sulfide and ammonium hydroxide in alcohol.

The introduction of substituents —POXY and —COR takes place according to usual methods, for example, in the presence of a base such as organic amines and a transition metal catalyst such as tetrakis-(triphenylphosphin)-palladium(O) at higher temperature in polar solvents such as dimethylformamide or cyclic or acyclic ethers or halogenated hydrocarbons.

The optionally subsequent saponification of an ester group can take place in a basic or preferably acidic manner, by hydrolyzing the reaction mixture at a higher temperature up to the boiling temperature in the presence of acids, such as highly concentrated aqueous hydrochloric acid in solvents such as, for example, trifluoroacetic acid or alcohols. Phosphonic acid esters are preferably hydrolyzed by heating in highly concentrated aqueous acids such as, for example, concentrated hydrochloric acid or by treatment with trimethylsilyl halide and subsequent treatment with water.

The esterification of the carboxylic acid or phosphonic acid takes place in a way known in the art with the corresponding alcohol in acid or in the presence of an activated acid derivative. As activated acid derivatives, for example, acid chloride, acid imidazolide or acid anhydride are suitable. In the phosphonic acids, the esterification can be achieved by reaction with orthoesters, optionally by the addition of catalysts such as p-toluenesulfonic acid.

The amidation takes place on the free acids or on their reactive derivatives such as, for example, acid chlorides, mixed anhydrides, imidazolides or azides by reaction with the corresponding amines at room temperature.

Many known halogenation methods, such as, e.g., electrophilic aromatic substitution, are suitable for introduction of a halogen radical. For example, the iodization with iodine/iodic acid in glacial acetic acid is possible according to a process of Wirth et al. [Liebigs Ann. Chem. 634, 84 (1960)] or with N-iodosuccinimide.

The introduction of an $NO_2$ group is possible by a series of known nitration methods. For example, nitration can be performed with nitronium tetrafluoroborate in inert solvents, such as halogenated hydrocarbons or in sulfolane or glacial acetic acid or by nitrating acid in concentrated sulfuric acid as solvent at temperatures between 0° C. and 30° C.

The reduction of the nitro group to the amino group takes place catalytically in polar solvents at room temperature or higher temperature under hydrogen pressure. Metals such as Raney nickel or noble metal catalysts such as palladium or platinum optionally in the presence of barium sulfate or on vehicles are suitable as catalysts. Instead of hydrogen, ammonium formate can also be used in a known way. Reducing agents such as tin-II-chloride or titanium-III-chloride can also be used as complex metal hydrides optionally in the presence of heavy metal salts. The ester group can be advantageously introduced before the reduction. Nitro groups can also be selectively reduced in the usual way with $Na_2S$ or sodium dithionite.

If an alkylation of an amino group is desired, then alkylation can be performed according to usual methods, for example, with alkyl halides or according to the Mitsonubo variant by reaction with an alcohol in the presence of triphenylphosphine and azodicarboxylic acid ester or the amine can be subjected to a reductive amination with aldehydes or ketones optionally in succession with two different carbonyl compounds, in which the mixed derivatives are obtained (literature, e.g., Verardo et al. Synthesis 1993, 121; Synthesis 1991, 447; Kawaguchi, Synthesis 1985, 701; Micovic et al. Synthesis 1991, 1043).

The acylation of an amino group can take place in the usual way, for example, with acid halide or acid anhydride optionally in the presence of a base such as dimethylaminopyridine in solvents such as methylene chloride, tetrahydrofuran or pyridine or according to the Scotten Baumann reaction.

The introduction of the cyano group can take place with the help of the Sandmeyer reaction; for example, the diazonium salts, intermediately formed from the amino compounds with nitrites, can be reacted with alkali cyanides in the presence of Cu—I-cyanide.

The introduction of the halogens chlorine, bromine or iodine by the amino group can also take place, for example, according to Sandmeyer, by the diazonium salts that are formed intermediately with nitrites reacting with Cu(I) chloride or Cu(I)bromide in the presence of the corresponding acid (hydrochloric acid or hydrobromic acid) or with potassium iodide. If, instead of a nitrite, an organic nitrous acid ester is used, the halogens can be introduced, e.g., by the addition of methylene iodide or tetrabromomethane.

The introduction of fluorine is possible, for example, by Balz Schiemann reaction of the diazonium tetrafluoroborate.

The nucleophilic substitution is performed according to methods known in the literature in the presence of a base and can be fostered by an activating electron-attracting group such as, e.g., nitro, cyano, trifluoromethyl preferably in ortho position. As nucleophiles, for example, primary and secondary amines, N-containing saturated or unsaturated heterocycles, cyanides, alcoholates, i.a., are suitable. The reaction can be performed in polar solvents such as alcohols, halogenated hydrocarbons, dimethylsulfoxide, dimethylacetamide, acetonitrile or water or without solvents. As bases, inorganic bases such as alkali or alkaline-earth hydroxides or carbonates or organic bases such as cyclic, acyclic and aromatic amines, such as DBU, Hünig base, pyridine or dimethylaminopyridine are suitable.

In the case of amines, the nucleophile itself can be used in excess as base and optionally it is possible to work without further solvent or under pressure.

The mixtures of isomers can be separated according to usual methods such as, for example, crystallization, chromatography or salt formation in the enantiomers or E/Z isomers.

The production of the salts takes place in the usual way, by mixing a solution of the compound of formula I with the equivalent amount or an excess of an alkali or alkaline-earth compound, which optionally is in solution, and the precipitate being separated or the solution being worked up in the usual way.

If the production of the starting compounds is not described, the latter are known or can be produced analogously to known compounds, for example, according to WO 93/08173 or processes described here.

The following examples are to explain the process according to the invention:

EXAMPLE 1 a) 1-(2,2,2-Trichloroethoxycarbonyl)-6-trifluoromethyl-1,2-dihydroquinoline-2-phosphonic acid diethyl ester 41.4 g of 6-trifluoromethylquinoline is introduced into 250 ml of acetonitrile at 0° C. 29 ml of chloroformic acid-2,2,2-trichloroethyl ester is rapidly instilled and the mixture is stirred for 30 minutes. 36.4 ml of triethylphosphite is instilled and 49.8 g of sodium iodide is added in portions. It is heated for 10 minutes to 50° C., the solution is concentrated by evaporation, mixed with 400 ml of water and extracted four times with 400 ml of ethyl acetate each. The crude product is purified by column chromatography and recrystallized from isopropyl ether.

Melting point: 71° C.

b) 1-(2,2,2-Trichloroethoxycarbonyl)-6-trifluoromethyl-1,2,3,4-tetrahydroquinoline-2-phosphonic acid diethyl ester 71.6 g of 1-(2,2,2-trichloroethoxycarbonyl)-6-trifluoromethyl-1,2-dihydroquinoline-2-phosphonic acid diethyl ester is dissolved in 800 ml of ethanol, mixed with 3.6 g of platinum(IV)-oxide and hydrogenated at normal pressure. It is filtered, concentrated by evaporation and recrystallized from isopropyl ether.

Melting point: 84° C.

c) 6-Trifluoromethyl-1,2,3,4-tetrahydroquinoline-2-phosphonic acid diethyl ester 15.4 g of 1-(2,2,2-trichloroethoxycarbonyl)-6-trifluoromethyl-1,2,3,4-tetrahydroquinoline-2-phosphonic acid diethyl ester is dissolved in 400 ml of methanol, mixed with 7.2 g of zinc powder and stirred under nitrogen for 1.5 hours at 90° C. It is filtered on diatomaceous earth and the filtrate is concentrated by evaporation. The crude product is purified by column chromatography and recrystallized from isopropyl ether.

Melting point: 129° C.

d) 1-Ethoxyoxalyl-6-trifluoromethyl-1,2,3,4-tetrahydroquinoline-2-phosphonic acid diethyl ester 5.39 g of 6-trifluoromethyl-1,2,3,4-tetrahydroquinoline-2-phosphonic acid diethyl ester is dissolved in 100 ml of tetrahydrofuran. 0.56 g of sodium hydride is added to it under nitrogen and with ice cooling. After 30 minutes at +5° C., 2 ml of oxalic acid ethyl ester chloride is instilled in it and the mixture is stirred overnight at room temperature. It is filtered on diatomaceous earth and the filtrate is concentrated by evaporation. The crude product is purified by column chromatography and recrystallized from isopropyl ether.

e) 1-Ethoxyoxalyl-8-nitro-6-trifluoromethyl-1,2,3,4-tetrahydroquinoline-2-phosphonic acid diethyl ester 5.25 g of 1-ethoxyoxalyl-6-trifluoromethyl-1,2,3,4-tetrahydroquinoline-2-phosphonic acid diethyl ester is dissolved in 100 ml of methylene chloride and mixed with 4.78 g of nitronium tetrafluoroborate. It is stirred for 23 hours at room temperature. The solution is washed twice with 40 ml of 5% sodium bicarbonate solution each and concentrated by evaporation.

f) 9-Trifluoromethyl-2,3-dioxo-1,2,3,5,6,7-hexahydro-pyrido[1,2,3-de]quinoxaline-5-phosphonic acid diethyl ester 6.27 g of 1-ethoxyoxalyl-8-nitro-6-trifluoromethyl-1,2,3,4-tetrahydroquinoline-2-phosphonic acid diethyl ester is dissolved in 100 ml of glacial acetic acid and mixed with 13 g of iron powder. The mixture is stirred for one hour at 90° C. After cooling to room temperature, it is suctioned off, the residue is taken up in 400 ml of ethyl acetate and the suspension is suctioned off again. The filtrate is washed with 50 ml of 5% sodium bicarbonate solution, dried on magnesium sulfate and concentrated by evaporation. The crude product is purified by column chromatography and recrystallized from ethyl acetate. 2.31 g of 9-trifluoromethyl-2,3-dioxo-1,2,3,5,6,7-hexahydro-pyrido[1,2,3-de]quinoxaline-5-phosphonic acid diethyl ester of melting point 161° C. is obtained.

Produced analogously is:
9-Chloro-2,3-dioxo-1,2,3,5,6,7-hexahydro-pyrido[1,2,3-de]quinoxaline-5-phosphonic acid diethyl ester
Melting point: 173° C.

Produced in a basically analogous way are:
9-Nitro-2,3-dioxo-1,2,3,5,6,7-hexahydro-pyrido[1,2,3-de]quinoxaline-5-phosphonic acid-diethyl ester
9-cyano-2,3-dioxo-1,2,3,5,6,7-hexahydro-pyrido[1,2,3-de]quinoxaline-5-phosphonic acid-dimethyl ester

EXAMPLE 2

9-Trifluoromethyl-2,3-dioxo-1,2,3,5,6,7-hexahydro-pyrido[1,2,3-de]quinoxaline-5-phosphonic acid 1.63 g of 9-trifluoromethyl-2,3-dioxo-1,2,3,5,6,7-hexahydro-pyrido[1,2,3-de]quinoxaline-5-phosphonic acid diethyl ester is introduced into 40 ml of acetonitrile under nitrogen at room temperature. 3.63 ml of trimethylsilylbromide is rapidly instilled. The solution is stirred for 20 hours at room temperature and concentrated by evaporation. The residue is suspended in 50 ml of water, suctioned off and washed with water. The residue is dried at 105° C. and 0.7 torr. 1.12 g of 9-trifluoromethyl-2,3-dioxo-1,2,3,5,6,7-hexahydro-pyrido[1,2,3-de]quinoxaline-5-phosphonic acid of melting point 262° C. is obtained.

Produced analogously are:
9-Chloro-2,3-dioxo-1,2,3,5,6,7-hexahydro-pyrido[1,2,3-de]quinoxaline-5-phosphonic acid
Melting point: 305° C.
9-nitro-2,3-dioxo-1,2,3,5,6,7-hexahydro-pyrido[1,2,3-de]quinoxaline-5-phosphonic acid
9-cyano-2,3-dioxo-1,2,3,5,6,7-hexahydro-pyrido[1,2,3-de]quinoxaline-5-phosphonic acid
9-trifluoromethyl-2,3-dioxo-1,2,3,5,6,7-hexahydro-pyrido[1,2,3-de]quinoxaline-6-phosphonic acid
Melting point: 294°–295° C.
9-cyano-2,3-dioxo-1,2,3,5,6,7-hexahydro-pyrido[1,2,3-de]quinoxaline-7-carboxylic acid
9-chloro-2,3-dioxo-1,2,3,5,6,7-hexahydro-pyrido[1,2,3-de]quinoxaline-7-phosphonic acid
9-trifluoromethyl-2,3-dioxo-1,2,3,5,6,7-hexahydro-pyrido[1,2,3-de]quinoxaline-7-phosphonic acid
Melting point: from 235° C. with decomposition
8-nitro-9-trifluoromethyl-2,3-dioxo-1,2,3,5,6,7-hexahydro-pyrido[1,2,3-de]quinoxaline-5-phosphonic acid
Melting point: 318° C. with decomposition
9-chloro-8-nitro-2,3-dioxo-1,2,3,5,6,7-hexahydro-pyrido[1,2,3-de]quinoxaline-5-phosphonic acid
9-trifluoromethyl-8-piperidino-2,3-dioxo-1,2,3,5,6,7-hexahydro-pyrido[1,2,3-de]quinoxaline-5-phosphonic acid
8-amino-9-trifluoromethyl-2,3-dioxo-1,2,3,5,6,7-hexahydro-pyrido[1,2,3-de]quinoxaline-5-phosphonic acid
8-fluoro-9-trifluoromethyl-2,3-dioxo-1,2,3,5,6,7-hexahydro-pyrido[1,2,3-de]quinoxaline-5-phosphonic acid
8-morpholino-9-trifluoromethyl-2,3-dioxo-1,2,3,5,6,7-hexahydro-pyrido[1,2,3-de]quinoxaline-5-phosphonic acid
2,3-dioxo-1,2,3,5,6,7-hexahydro-benzo[h]pyrido[1,2,3-de]quinoxaline-5-phosphonic acid
5,6-dioxo-1,2,3,5,6,7-hexahydro-benzo[g]pyrido[1,2,3-de]quinoxaline-3-phosphonic acid
9-chloro-2,3-dioxo-1,2,3,5,6,7-hexahydro-pyrido[1,2,3-de]quinoxaline-5-carboxylic acid
8-[1-(1,2,4-Triazolyl)]-9-trifluoromethyl-2,3-dioxo-1,2,3,5,6,7-hexahydro-pyrido[1,2,3-de]quinoxaline-5-phosphonic acid
8-(1-pyrrolyl)-9-trifluoromethyl-2,3-dioxo-1,2,3,5,6,7-hexahydro-pyrido[1,2,3-de]quinoxaline-5-phosphonic acid of melting point >300° C. (decomposition)

EXAMPLE 3 a) 3-Bromo-6-trifluoromethyl-quinoline 19.7 g of 6-trifluoromethyl-quinoline is introduced into 200 ml of tetrachloromethane. 5.2 ml of bromine is instilled and the solution is refluxed for one hour. Within twenty minutes, 7.9 g of pyridine in 8 ml of tetrachloromethane is instilled in the boiling solution. After one hour, it is allowed to cool, decanted from the precipitated salt and the solution is concentrated by evaporation. After column chromatography, 14.6 g of 3-bromo-6-trifluoromethyl-quinoline of melting point 79° C. is obtained.

b) 6-Trifluoromethyl-quinoline-3-phosphonic acid diethyl ester 1.44 g of tetrakis-(triphenylphosphine)-palladium(O) are introduced in 16 ml of toluene, 3.8 ml of triethylamine and 3.6 ml of diethylphosphite at room temperature under nitrogen and mixed with 6.90 g of 3-bromo-6-trifluoromethyl-quinoline. It is stirred for two hours at 90° C. bath temperature. The mixture is diluted with ether, suctioned off and the filtrate is concentrated by evaporation. After column chromatography, 8.3 g of 6-trifluoromethyl-quinoline-3-phosphonic acid diethyl ester of melting point 69° C. is obtained.

c) 6-Trifluoromethyl-1,2,3,4-tetrahydroquinoline-3-phosphonic acid diethyl ester 6.66 g of 6-trifluoromethyl-quinoline-3-phosphonic acid diethyl ester is dissolved in 70 ml of glacial acetic acid and hydrogenated on platinum dioxide at room temperature under normal pressure. After column chromatography, 3.52 g of 6-trifluoromethyl-1,2,3,4-tetrahydroquinoline-3-phosphonic acid diethyl ester of melting point 112° C. is obtained.

d) 1-Ethoxyoxalyl-6-trifluoromethyl-1,2,3,4-tetrahydroquinoline-3-phosphonic acid diethyl ester 4.04 g of 6-trifluoromethyl-1,2,3,4-tetrahydroquinoline-3-phosphonic acid diethyl ester is introduced into 80 ml of tetrahydrofuran under nitrogen and ice cooling. 0.43 g of 80% sodium hydride is added with stirring. After 30 minutes, 1.6 ml of oxalic acid ethyl ester chloride is instilled in it. It is stirred for two hours at room temperature, filtered on diatomaceous earth and concentrated by evaporation. After column chromatography, 4.87 g of 1-ethoxyoxalyl-6-trifluoromethyl-1,2,3,4-tetrahydroquinoline-3-phosphonic acid diethyl ester is obtained as colorless oil.

e) 1-Ethoxyoxalyl-8-nitro-6-trifluoromethyl-1,2,3,4-tetrahydroquinoline-3-phosphonic acid diethyl ester 4.37 g of 1-ethoxyoxalyl-6-trifluoromethyl-1,2,3,4-tetrahydroquinoline-3-phosphonic acid diethyl ester is introduced into 100 ml of dichloromethane and mixed with 3.98 g of nitronium tetrafluoroborate. It is stirred for 24 hours at room temperature, washed twice with 30 ml of 5% sodium bicarbonate solution each and concentrated by evaporation. After column chromatography, 4.25 g of 1-ethoxyoxalyl-8-nitro-6-trifluoromethyl-1,2,3,4-tetrahydroquinoline-3-phosphonic acid diethyl ester of melting point 70°–72° C. is obtained.

f) 9-Trifluoromethyl-2,3-dioxo-1,2,3,5,6,7-hexahydro-pyrido[1,2,3-de]quinoxaline-6-phosphonic acid diethyl ester 4.25 g of 1-ethoxyoxalyl-8-nitro-6-trifluoromethyl-1,2,3,4-tetrahydroquinoline-3-phosphonic acid diethyl ester is dissolved in 75 ml of glacial acetic acid and mixed with 8.5 g of iron powder. It is stirred for one hour at 90° C. bath temperature, suctioned off and the filtrate concentrated by evaporation. After column chromatography and recrystallization from ethyl acetate, 1.45 g of 9-trifluoromethyl-2,3-dioxo-1,2,3,5,6,7-hexahydro-pyrido[1,2,3-de]quinoxaline-6-phosphonic acid diethyl ester of melting point 253° C. is obtained.

Produced in a basically analogous way is:
9-Chloro-2,3-dioxo-1,2,3,5,6,7-hexahydro-pyrido[1,2,3-de]quinoxaline-6-carboxylic acid ethyl ester

EXAMPLE 4 a) 4-Hydroxy-6-trifluoromethyl-quinoline

This compound was produced from 4-trifluoromethylaniline analogously to the process described in J. of the Am. Chem. Soc. 68, 2685–2688 (1946).

b) 4-Bromo-6-trifluoromethyl-quinoline 25.8 g of phosphoroxy bromide is introduced at room temperature and with slow heating is mixed in portions with 6.39 g of 4-hydroxy-6-trifluoromethyl-quinoline. It is stirred for one hour at 90° C., decomposed with 120 ml of ice water and adjusted alkaline with 50 ml of 32% sodium hydroxide solution. After one hour, the precipitated product is suctioned off, washed with water and dried. The crystals are dissolved in hot hexane, the insoluble parts filtered off and the filtrate concentrated by evaporation. 7.34 g of 4-bromo-6-trifluoromethyl-quinoline of melting point 56° C. is obtained.

c) 6-Trifluoromethyl-quinoline-4-phosphonic acid diethyl ester 1.73 g of tetrakis-(triphenylphosphine)-palladium(O) in 20 ml of toluene is mixed with 4.6 ml of triethylamine, 4.3 ml of diethylphosphite and 8.28 g of 4-bromo-6-trifluoromethyl-quinoline and stirred for three hours at 90° C. Another 0.17 g of tetrakis-(triphenylphosphine)-palladium(O) and 0.4 ml of triethylamine and diethylphosphite each are added and stirred for one hour at 90° C. After cooling, it is diluted with ether, suctioned off, washed with ether and the filtrate is concentrated by evaporation. The product is purified by column chromatography. 8.33 g of 6-trifluoromethyl-quinoline-4-phosphonic acid diethyl ester is obtained as colorless oil.

d) 6-Trifluoromethyl-1,2,3,4-tetrahydroquinoline-4-phosphonic acid diethyl ester 8.32 g of 6-trifluoromethyl-quinoline-4-phosphonic acid diethyl ester is dissolved in 100 ml of glacial acetic acid, mixed with 1.0 g of platinum dioxide and hydrogenated at room temperature. After column chromatography, 5.44 g of 6-trifluoromethyl-1,2,3,4-tetrahydroquinoline-4-phosphonic acid diethyl ester of melting point 94° C. is obtained.

e) 1-Ethoxyoxalyl-6-trifluoromethyl-1,2,3,4-tetrahydroquinoline-4-phosphonic acid diethyl ester 5.05 g of 6-trifluoromethyl-1,2,3,4-tetrahydroquinoline-4-phosphonic acid diethyl ester is introduced in 100 ml of tetrahydrofuran under nitrogen and mixed with 0.54 g of 80% sodium hydride. After 30 minutes, 1.9 ml of oxalic acid ethyl ester chloride is instilled at room temperature. It is stirred for 15 hours at room temperature, filtered on diatomaceous earth and concentrated by evaporation. After column chromatography, 5.99 g of 1-ethoxyoxalyl-6-trifluoromethyl-1,2,3,4-tetrahydroquinoline-4-phosphonic acid diethyl ester is obtained as colorless oil.

f) 1-Ethoxyoxalyl-8-nitro-6-trifluoromethyl-1,2,3,4-tetrahydroquinoline-4-phosphonic acid diethyl ester 5.68 g of 1-ethoxyoxalyl-6-trifluoromethyl-1,2,3,4-tetrahydroquinoline-4-phosphonic acid diethyl ester is dissolved in 100 ml of dichloromethane and mixed with 5.18 g of nitronium tetrafluoroborate. The solution is stirred for 20 hours at room temperature, washed with 5% sodium bicarbonate solution and concentrated by evaporation. After column chromatography, 5.34 g of 1-ethoxyoxalyl-8-nitro-6-trifluoromethyl-1,2,3,4-tetrahydroquinoline-4-phosphonic acid diethyl ester is obtained as colorless oil.

g) 9-Trifluoromethyl-2,3-dioxo-1,2,3,5,6,7-hexahydro-pyrido[1,2,3-de]quinoxaline-7-phosphonic acid diethyl ester 5.30 g of 1-ethoxyoxalyl-8-nitro-6-trifluoromethyl-1,2,3,4-tetrahydroquinoline-4-phosphonic acid diethyl ester is introduced into 90 ml of glacial acetic acid, mixed with 10.6 g of iron powder and stirred for one hour at 90° C. The suspension is suctioned off warm, washed again with ethyl acetate and the filtrate is concentrated by evaporation. The product is purified by column chromatography and recrystallized from ethyl acetate. 2.47 g of 9-trifluoromethyl-2,3-dioxo-1,2,3,5,6,7-hexahydro-pyrido[1,2,3-de]quinoxaline-7-phosphonic acid diethyl ester of melting point 250° C. is obtained.

EXAMPLE 5

8-Nitro-9-trifluoromethyl-2,3-dioxo-1,2,3,5,6,7-hexahydro-pyrido[1,2,3-de]quinoxaline-5-phosphonic acid diethyl ester 812 mg of 9-trifluoromethyl-2,3-dioxo-1,2,3,5,6,7-hexahydro-pyrido[1,2,3-de]quinoxaline-5-phosphonic acid diethyl ester is dissolved in 15 ml of dichloromethane and mixed with 531 mg of nitronium tetrafluoroborate at room temperature. It is stirred for 15 hours and concentrated by evaporation. The residue is taken up in ethyl acetate and washed with 5% sodium bicarbonate solution. After column chromatography, 470 mg of 8-nitro-9-trifluoromethyl-2,3-dioxo-1,2,3,5,6,7-hexahydro-pyrido[1,2,3-de]quinoxaline-5-phosphonic acid diethyl ester of melting point 254° C. is obtained.

EXAMPLE 6

8-Amino-9-trifluoromethyl-2,3-dioxo-1,2,3,5,6,7-hexahydro-pyrido[1,2,3-de]quinoxaline-5-phosphonic acid diethyl ester 226 mg of 8-nitro-9-trifluoromethyl-2,3-dioxo-1,2,3,5,6,7-hexahydro-pyrido[1,2,3-de]quinoxaline-5-phosphonic acid diethyl ester is dissolved in 20 ml of ethanol, mixed with 50 mg of 10% palladium on activated carbon and hydrogenated at room temperature and under normal pressure. After suctioning off the catalyst, it is concentrated by evaporation and recrystallized from ethanol. 146 mg of 8-amino-9-trifluoromethyl-2,3-dioxo-1,2,3,5,6,7-hexahydro-pyrido[1,2,3-de]quinoxaline-5-phosphonic acid diethyl ester of melting point 242° C. (with decomposition) is obtained.

EXAMPLE 7

8-(1-Pyrrolyl)-9-trifluoromethyl-2,3-dioxo-1,2,3,5,6,7-hexahydro-pyrido[1,2,3-de]quinoxaline-5-phosphonic acid diethyl ester 211 mg of 8-amino-9-trifluoromethyl-2,3-dioxo-1,2,3,5,6,7-hexahydro-pyrido[1,2,3-de]quinoxaline-5-phosphonic acid diethyl ester and 66 mg of 2,5-dimethoxytetrahydrofuran are reacted for one hour at 140° C. bath temperature. After recrystallization from ethanol, 123 mg of 8-(1-pyrrolyl)-9-trifluoromethyl-2,3-dioxo-1,2,3,5,6,7-hexahydro-pyrido[1,2,3-de]quinoxaline-5-phosphonic acid diethyl ester of melting point 268° C. is obtained.

EXAMPLE 8

8-Iodo-9-trifluoromethyl-2,3-dioxo-1,2,3,5,6,7-hexahydro-pyrido[1,2,3-de]quinoxaline-5-phosphonic acid 406 mg of 9-trifluoromethyl-2,3-dioxo-1,2,3,5,6,7-hexahydro-pyrido[1,2,3-de]quinoxaline-5-phosphonic acid diethyl ester in 2 ml of glacial acetic acid is mixed with 0.05 ml of water, 0.025 ml of concentrated sulfuric acid, 178 mg of iodine and 70 mg of iodic acid and stirred for 15 hours at 80° C. bath temperature. After concentration by evaporation, it is mixed with water and the product is suctioned off. 60 mg of 8-iodo-9-trifluoromethyl-2,3-dioxo-1,2,3,5,6,7-hexahydro-pyrido[1,2,3-de]quinoxaline-5-phosphonic acid of melting point 307° C. (with decomposition) is obtained.

EXAMPLE 9

8-Iodo-9-trifluoromethyl-2,3-dioxo-1,2,3,5,6,7-hexahydro-pyrido[1,2,3-de]quinoxaline-5-phosphonic acid diethyl ester 100 mg of 8-amino-9-trifluoromethyl-2,3-dioxo-1,2,3,5,6,7-hexahydro-pyrido[1,2,3-de]quinoxaline-5-phosphonic acid diethyl ester is taken up in 8 ml of ethanolic hydrochloric acid and concentrated by evaporation, and the hydrochloride is taken up in 6 ml of dimethylformamide and 3 ml of methylene iodide and mixed at 80° C. bath temperature with 0.08 ml of i-amyl nitrite. After 3 hours of stirring at this temperature, the batch is concentrated by evaporation in a vacuum. 95 mg of 8-iodo-9-trifluoromethyl-2,3-dioxo-1,2,3,5,6,7-hexahydro-pyrido[1,2,3-de]quinoxaline-5-phosphonic acid diethyl ester is obtained.

Produced in a basically analogous way by diazotization in an aqueous medium are:

8-Fluoro-9-trifluoromethyl-2,3-dioxo-1,2,3,5,6,7-hexahydro-pyrido[1,2,3-de]quinoxaline-5-phosphonic acid diethyl ester 9-cyano-2,3-dioxo-1,2,3,5,6,7-hexahydro-pyrido[1,2,3-de]quinoxaline-5-carboxylic acid methyl ester.

EXAMPLE 10

8-(Piperidin-1-yl)-9-trifluoromethyl-2,3-dioxo-1,2,3,5,6,7-hexahydro-pyrido[1,2,3-de]quinoxaline-5-phosphonic acid diethyl ester At 0° C., a solution of 0.15 ml of a 25% aqueous solution of glutaric dialdehyde and 0.45 ml of 3M sulfuric acid in 3 ml of tetrahydrofuran:methanol=2:3 are instilled in a suspension of 110 mg of 8-amino-9-trifluoromethyl-2,3-dioxo-1,2,3,5,6,7-hexahydro-pyrido[1,2,3-de]quinoxaline-5-phosphonic acid diethyl ester and 30 mg of sodium borohydride tablets in 3 ml of tetrahydrofuran. After the reaction dies down, 30 mg of sodium borohydride tablets are thrown in again and then stirred for 1 hour at room temperature. Then, it is adjusted neutral with sodium hydroxide solution and shaken out with ethyl acetate. The ethyl acetate phase is dried, filtered and concentrated by evaporation. After chromatography on silica gel with toluene:glacial acetic acid:water=10:10:1, 50 mg of 1-[(6-trifluoromethyl-7-[piperidin-1-yl]quinoxaline-2,3-dion)-1-yl]-ethanephosphonic acid diethyl ester is obtained.

Produced in a basically analogous way is:

8-Morpholino-9-trifluoromethyl-2,3-dioxo-1,2,3,5,6,7-hexahydro-pyrido[1,2,3-de]quinoxaline-5-phosphonic acid diethyl ester.

EXAMPLE 11

8-(1-Imidazolyl)-9-trifluoromethyl-2,3-dioxo-1,2,3,5,6,7-hexahydro-pyrido[1,2,3-de]quinoxaline-5-phosphonic acid 150 mg of 1-8-fluoro-9-trifluoromethyl-2,3-dioxo-1,2,3,5,6,7-hexahydro-pyrido[1,2,3-de]quinoxaline-5-phosphonic acid diethyl ester is stirred together with 600 mg of imidazole for 2 hours at 160° C. bath temperature. The reaction mixture is then refluxed in 10 ml of concentrated hydrochloric acid for 1.5 hours, concentrated by evaporation and taken up in 5 ml of water and suctioned off. 100 mg of 8-(1-imidazolyl)-9-trifluoromethyl-2,3-dioxo-1,2,3,5,6,7-hexahydro-pyrido[1,2,3-de]quinoxaline-5-phosphonic acid is obtained.

We claim:

1. Compounds of formula I

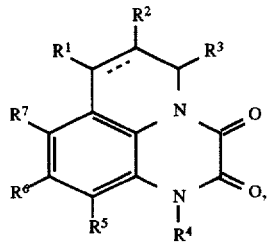

in which

R¹, R² and R³ each mean hydrogen, —POXY, or halogen but are not simultaneously hydrogen, R⁴ means hydrogen or OH, R⁵, R⁶ and R⁷ are the same or different and mean hydrogen, halogen, nitro, NR¹²R¹³, cyano, CF₃, $C_{1-6}$ alkyl, $C_{1-4}$ alkoxy or R⁵ and R⁶ or R⁶ and R⁷ represent a fused benzene ring or a single or double bond, and X and Y are the same or different and mean hydroxy, $C_{1-6}$ alkoxy, —O—(CH₂)ₙ—O—, $C_{1-4}$ alkyl or NR⁹R¹⁰ and n is 1, 2 or 3 and R means hydroxy, $C_{1-6}$ alkoxy or NR⁹R¹⁰ and R⁹ and R¹⁰, R¹² and R¹³ are the same or different and mean hydrogen, —CO—$C_{1-6}$ alkyl, phenyl or $C_{1-6}$ alkyl, which optionally can be substituted with $C_{1-4}$ alkoxy or an amino group that is optionally mono- or disubstituted with $C_{1-4}$ alkyl, or together with the nitrogen atom can form a saturated 5- to 7-membered heterocycle, which can contain another oxygen, sulfur or nitrogen atom and can optionally be substituted, or form an unsaturated 5-membered heterocycle, which contains 1–3N atoms and can be substituted, as well as their isomers or salts.

2. A compound selected from 8-(1-Imidazolyl)-9-trifluoromethyl-2,3-dioxo-1,2,3,5,6,7-hexahydro-pyrido[1,2,3-de]quinoxaline-5-phosphonic acid 8-iodo-9-trifluoromethyl-2,3-dioxo-1,2,3,5,6,7-hexahydro-pyrido[1,2,3-de]quinoxaline-5-phosphonic acid 8-(1-pyrrolyl)-9-trifluoromethyl-2,3-dioxo-1,2,3,5,6,7-hexahydro-pyrido[1,2,3-de]quinoxaline-5-phosphonic acid 8-morpholino-9-trifluoromethyl-2,3-dioxo-1,2,3,5,6,7-hexahydro-pyrido[1,2,3-de]quinoxaline-5-phosphonic acid 8-amino-9-trifluoromethyl-2,3-dioxo-1,2,3,5,6,7-hexahydro-pyrido[1,2,3-de]quinoxaline-5-phosphonic acid 9-trifluoromethyl-2,3-dioxo-1,2,3,5,6,7-hexahydro-pyrido[1,2,3-de]quinoxaline-6-phosphonic acid 9-chloro-2,3-dioxo-1,2,3,5,6,7-hexahydro-pyrido[1,2,3-de]quinoxaline-5-phosphonic acid 9-trifluoromethyl-2,3-dioxo-1,2,3,5,6,7-hexahydro-pyrido[1,2,3-de]quinoxaline-5-phosphonic acid 9-trifluoromethyl-2,3-dioxo-1,2,3,5,6,7-hexahydro-pyrido[1,2,3-de]quinoxaline-7-phosphonic acid 9-trifluoromethyl-2,3-dioxo-1,2,3,5,6,7-hexahydro-pyrido[1,2,3-de]quinoxaline-5-phosphonic acid diethyl ester and mixtures thereof.

3. Pharmaceutical agents based on the compounds according to claim 1.

4. Process for the production of the compounds of formula I of claim 1, characterized in that a) a compound of formula II

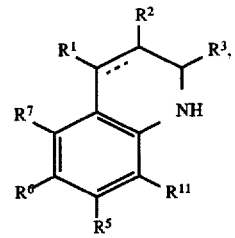

in which

R¹¹ is H, NO₂ or —NH—R⁴ and R¹ to R⁷ have the above-mentioned meaning, is reacted with oxalic acid or reactive oxalic acid derivatives and is optionally cyclized after introduction and reduction of the NO₂ group and, if R¹, R² and/or R³ mean halogen, is optionally reacted or carbonylated with XYP—O—$C_{1-4}$ alkyl or b) a compound of formula III

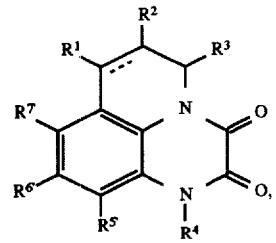

in which

R¹ to R⁴ have the above-mentioned meaning, and R⁵', R⁶' or R⁷' means hydrogen or an electron-attracting group, is halogenated or nitrated and then optionally an ester group is then saponified or an acid group is esterified or amidated or a nitro group is reduced to the amino group or an amino group is alkylated or acylated or an amino group is exchanged for halogen or cyano or a nitro group or halogen is introduced or nucleophilically substituted or the isomers are separated or the salts are formed.

* * * * *